United States Patent
Etzel et al.

(10) Patent No.: US 9,492,771 B2
(45) Date of Patent: Nov. 15, 2016

(54) LIGAND GRAFT FUNCTIONALIZED SUBSTRATES

(75) Inventors: Mark R. Etzel, Madison, WI (US); Kannan Seshadri, Woodbury, MN (US); Jerald K. Rasmussen, Woodville, WI (US); Clinton P. Waller, Jr., White Bear Lake, MN (US); Douglas E. Weiss, Golden Valley, MN (US); Yi He, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1046 days.

(21) Appl. No.: 12/562,573

(22) Filed: Sep. 18, 2009

(65) Prior Publication Data

US 2010/0075131 A1    Mar. 25, 2010

(51) Int. Cl.
| | |
|---|---|
| B32B 3/00 | (2006.01) |
| B01D 39/16 | (2006.01) |
| C08J 7/18 | (2006.01) |
| C07K 1/34 | (2006.01) |

(52) U.S. Cl.
CPC ............ *B01D 39/1676* (2013.01); *C07K 1/34* (2013.01); *C08J 7/18* (2013.01); *C08J 2327/14* (2013.01); *Y10T 428/249978* (2015.04); *Y10T 428/249991* (2015.04); *Y10T 428/2935* (2015.01); *Y10T 442/2033* (2015.04); *Y10T 442/2525* (2015.04); *Y10T 442/60* (2015.04)

(58) Field of Classification Search
None
See application file for complete search history.

(56) References Cited

U.S. PATENT DOCUMENTS

| | | | |
|---|---|---|---|
| 1,529,256 A | | 3/1925 | Kelley |
| 2,945,006 A | | 7/1960 | Minsk |
| 3,352,424 A | * | 11/1967 | Guebert et al. .............. 502/62 |
| 4,157,418 A | | 6/1979 | Heilmann |
| 4,266,044 A | | 5/1981 | Timmerman |
| 4,439,322 A | | 3/1984 | Sonoda et al. |
| 4,529,256 A | | 7/1985 | Kretzschmar et al. |
| 4,563,388 A | | 1/1986 | Bonk et al. |
| 4,726,989 A | | 2/1988 | Mrozinski |
| 4,867,881 A | | 9/1989 | Kinzer |
| 5,120,594 A | | 6/1992 | Mrozinski |
| 5,142,010 A | | 8/1992 | Olstein |
| 5,260,360 A | | 11/1993 | Mrozinski et al. |
| 5,308,641 A | | 5/1994 | Cahalan et al. |
| 5,342,688 A | | 8/1994 | Kitchin |
| 5,429,629 A | | 7/1995 | Latimer |
| 5,506,279 A | | 4/1996 | Babu et al. |
| 5,531,900 A | | 7/1996 | Raghavan et al. |
| 5,547,576 A | | 8/1996 | Onishi et al. |
| 5,627,217 A | | 5/1997 | Rilling et al. |
| 5,736,051 A | | 4/1998 | Degen et al. |
| 5,782,908 A | | 7/1998 | Cahalan et al. |
| 5,804,263 A | | 9/1998 | Goldberg et al. |
| 5,866,113 A | | 2/1999 | Hendriks |
| 5,906,734 A | | 5/1999 | Girot et al. |
| 5,914,182 A | | 6/1999 | Drumheller |
| 5,962,544 A | | 10/1999 | Waller, Jr. |
| 6,033,719 A | | 3/2000 | Keogh |
| 6,207,749 B1 | | 3/2001 | Mayes |
| 6,245,922 B1 | | 6/2001 | Heilmann et al. |
| 6,258,276 B1 | | 7/2001 | Mika et al. |
| 6,448,301 B1 | | 9/2002 | Gaddam et al. |
| 6,511,600 B1 | | 1/2003 | Ohtani |
| 6,635,104 B2 | | 10/2003 | Komkova et al. |
| 6,669,994 B2 | | 12/2003 | Swan et al. |
| 7,125,603 B2 | | 10/2006 | David et al. |
| 7,169,407 B1 | | 1/2007 | Miyata |
| 7,169,933 B2 | | 1/2007 | Benson et al. |
| 7,247,370 B2 | | 7/2007 | Childs et al. |
| 7,316,919 B2 | | 1/2008 | Childs et al. |
| 7,338,692 B2 | | 3/2008 | Smith et al. |
| 7,361,767 B2 | | 4/2008 | Benson et al. |
| 7,402,678 B2 | | 7/2008 | Benson et al. |
| 7,604,746 B2 | | 10/2009 | Childs et al. |
| 2002/0001834 A1 | | 1/2002 | Keogh |
| 2002/0142020 A1 | | 10/2002 | Woollven |
| 2003/0134551 A1 | | 7/2003 | Sugo |
| 2004/0203149 A1 | | 10/2004 | Childs et al. |
| 2005/0025911 A1 | | 2/2005 | Kasperchik |
| 2005/0118425 A1 | | 6/2005 | Childs et al. |
| 2005/0133441 A1 | | 6/2005 | Charkoudian |
| 2005/0142296 A1 | | 6/2005 | Lakshmi |
| 2006/0121217 A1 | | 6/2006 | Childs et al. |
| 2006/0165999 A1 | | 7/2006 | Fansler |
| 2007/0042198 A1 | | 2/2007 | Schonemyr |
| 2007/0065490 A1 | | 3/2007 | Schaberg et al. |

(Continued)

FOREIGN PATENT DOCUMENTS

| | | |
|---|---|---|
| EP | 1 228 756 | 8/2002 |
| JP | 07-138393 | 5/1995 |

(Continued)

OTHER PUBLICATIONS

PCT International Search Report, PCT/US2009/057465.
PCT International Search Report, PCT/US2009/057484.
Kawai, et al., "Protein binding to polymer brush, based on ion-exchange, hydrophobic, and affinity interactions," Journal of Chromatography B, vol. 790, Issues 1-2, pp. 131-142, 2003.
Ghosh, Raja, "Protein separation using membrane chromatography: opportunities and challenges," Journal of Chromatography A., vol. 952, Issues 1-2, pp. 13-27, 2002.
Kolarz, et al., "New selective resins with guanidyl groups," Reactive & Functional Polymers, vol. 36, (1998), pp. 185-195.
U.S. Appl. No. 12/562381 entitled, "Ligand Graft Functionalized Substrates" filed Sep. 18, 2009.
U.S. Appl. No. 61/057517 entitled, "Method of Making Ligand Functionalized Substrates" filed May 30, 2008.
U.S. Appl. No. 61/057523 entitled, "Ligand Functionalized Substrates" filed May 30, 2008.

(Continued)

*Primary Examiner* — Chinessa Adkins
(74) *Attorney, Agent, or Firm* — Kent S. Kokko

(57) ABSTRACT

Polyethyleneimine and polyalkylene biguanide ligand functionalized substrates, methods of making ligand functionalized substrates, and methods of using functionalized substrates are disclosed.

3 Claims, No Drawings

(56) References Cited

U.S. PATENT DOCUMENTS

| | | |
|---|---|---|
| 2007/0138084 A1 | 6/2007 | Galvin |
| 2007/0154651 A1 | 7/2007 | Weiss |
| 2007/0154703 A1 | 7/2007 | Waller et al. |
| 2008/0017578 A1 | 1/2008 | Childs et al. |
| 2008/0264867 A1 | 10/2008 | Mika et al. |
| 2009/0098359 A1 | 4/2009 | Waller, Jr. et al. |
| 2009/0176052 A1 | 7/2009 | Childs et al. |

FOREIGN PATENT DOCUMENTS

| | | |
|---|---|---|
| JP | 2003 301059 | 10/2003 |
| WO | WO 97/18904 | 5/1997 |
| WO | WO 99/32158 | 7/1999 |
| WO | WO 00/22032 | 4/2000 |
| WO | WO 01/17575 | 3/2001 |
| WO | WO 01/29118 | 4/2001 |
| WO | WO 01/96487 | 12/2001 |
| WO | WO 02/060509 | 8/2002 |
| WO | WO 03/008011 | 1/2003 |
| WO | WO 03/055923 | 7/2003 |
| WO | WO 2007/027858 | 3/2007 |
| WO | WO 2007/078878 | 7/2007 |
| WO | WO 2009/127285 | 10/2009 |

OTHER PUBLICATIONS

Mika, et al., "Acid/base properties of poly(4-vinylpyridine) anchored within microporous membranes," Journal of Membrane Science, vol. 152, pp. 129-140, 1999.

Mika et al., "Chemical valves based on poly(4-vinylpyridine)-filled microporous membranes," Journal of Membrane Science, vol. 153, pp. 45-56, 1999.

Suryanarayan, et al., "The effect of gel layer thickness on the salt rejection performance of polyelectrolyte gel-filled nanofiltration membranes," Journal of Membrane Science, vol. 290, pp. 196-206, 2007.

Zhang, et al., "pH Control of Transport through a Porous Membrane Self-Assembled with a Poly(acrylic acid) Loop Brush," Langmuir, vol. 17, pp. 8336-8340, 2001.

Kavakli, et al., "Radiation-induced grafting of dimethylaminoethylmethacrylate onto PE/PP nonwoven fabric," Science Direct, Nuclear Instruments and Methods in Physics Research B, vol. 265, pp. 204-207, 2007.

Ulbricht, Mathias, "Advanced functional polymer membranes," Science Direct, Polymer, vol. 47, pp. 2217-2262, 2006.

Osada, et al., "Control of Water Permeability by Mechanochemical Contraction of Poly(Methacrylic Acid)-Grafted Membranes," Journal of Membrane Science, vol. 27, pp. 327-338, 1986.

Ito, et al., "pH-Sensitive Gating by Conformational Change of a Polypeptide Brush Grafted onto a Porous Polymer Membrane," Journal of the American Chemical Society, vol. 119, pp. 1619-1623, 1997.

Zhou, et al., "Pore-filled nanofiltration membranes based on poly(2-acrylamido-2- methylpropanesulfonic acid) gels," Science Direct, Journal of Membrane Science, vol. 254, pp. 89-99, 2005.

Mika, et al., "Salt separation and hydrodynamic permeability of a porous membrane filled with pH-sensitive gel," Journal of Membrane Science, vol. 206, pp. 19-30, 2002.

Kim et al., "Diffusion and Flow through Polymer-Lined Micropores," Ind. Eng. Chem. Res., vol. 30, pp. 1008-1016, 1991.

Winnik, et al., "Polyacrylic acid pore-filled microporous membranes and their use in membrane-mediated synethesis of nanocrystalline ferrihydrite," Can. J. Chem., vol. 76, pp. 10-17, 1998.

Ulbricht, et al., "Porous Polypropylene Membranes with Different Carboxyl Polymer Brush Layers for Reversible Protein Binding via Surface-Initiated Graft Coplymerization," Chemical Mater, vol. 17, No. 10, pp. 2622-2631, 2005.

Buehler, et al., "Solvent Effects on the Permeability of Membrane-Supported Gels," Ind. Eng. Chem. Res., vol. 41, No. 3, pp. 464-472, 2002.

Kanani, et al., "Separation of human plasma proteins HAS and HIgG using high-capacity macroporous gel-filled membranes," Biochemical Engineering Journal, vol. 35, pp. 295-300, 2007.

Mika, et al., "Poly(4-vinylpyridine)-filled microfiltration membranes: physicochemical properties and morphology," Journal of Membrane Science, vol. 136, pp. 221-232, 1997.

Mika, et al., "Porous, polyelectrolyte-filled membranes: Effect of cross-linking on flux and separation," Journal of Membrane Science, vol. 135, pp. 81-92, 1997.

Childs, et al., "Nanofiltration using pore-filled membranes: effect of polyelectrolyte composition on performance," Separation and Purification Technology, vol. 22-23, pp. 507-517, 2001.

Mika, et al., "A new class of polyelectrolyte-filled microfiltration membranes with environmentally controlled porosity," Journal of Membrane Science, vol. 108, pp. 37-56, 1995.

* cited by examiner

LIGAND GRAFT FUNCTIONALIZED SUBSTRATES

CROSS-REFERENCE TO RELATED APPLICATIONS

This patent application claims the benefit of priority to U.S. provisional patent application Ser. No. 61/098,337 entitled "LIGAND GRAFT FUNCTIONALIZED SUBSTRATES", filed on Sep. 19, 2008, the subject matter of which is hereby incorporated by reference in its entirety.

TECHNICAL FIELD

The present disclosure relates to ligand-functionalized substrates, and methods for preparing the same. The functionalized substrates are useful in selectively binding and removing biological materials, such as viruses, from biological samples.

BACKGROUND

Detection, quantification, isolation and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic and in biomedical research. Biomacromolecules such as enzymes which are a special class of proteins capable of catalyzing chemical reactions are also useful industrially; enzymes have been isolated, purified, and then utilized for the production of sweeteners, antibiotics, and a variety of organic compounds such as ethanol, acetic acid, lysine, aspartic acid, and biologically useful products such as antibodies and steroids.

In their native state in vivo, structures and corresponding biological activities of these biomacromolecules are maintained generally within fairly narrow ranges of pH and ionic strength. Consequently, any separation and purification operation must take such factors into account in order for the resultant, processed biomacromolecule to have potency.

Chromatographic separation and purification operations can be performed on biological product mixtures, based on the interchange of a solute between a moving phase, which can be a gas or liquid, and a stationary phase. Separation of various solutes of the solution mixture is accomplished because of varying binding interactions of each solute with the stationary phase; stronger binding interactions generally result in longer retention times when subjected to the dissociation or displacement effects of a mobile phase compared to solutes which interact less strongly and, in this fashion, separation and purification can be effected.

Most current capture or purification chromatography is done via conventional column techniques. These techniques have severe bottlenecking issues in downstream purification, as the throughput using this technology is low. Attempts to alleviate these issues include increasing the diameter of the chromatography column, but this in turn creates challenges due to difficulties of packing the columns effectively and reproducibly. Larger column diameters also increase the occurrence of problematic channeling. Also, in a conventional chromatographic column, the absorption operation is shut down when a breakthrough of the desired product above a specific level is detected. This causes the dynamic or effective capacity of the adsorption media to be significantly less than the overall or static capacity. This reduction in effectiveness has severe economic consequences, given the high cost of some chromatographic resins.

Polymeric resins are widely used for the separation and purification of various target compounds. For example, polymeric resins can be used to purify or separate a target compound based on the presence of an ionic group, based on the size of the target compound, based on a hydrophobic interaction, based on a specific receptor-ligand affinity interaction, or based on the formation of a covalent bond, or a combination of the aforementioned interactions. There is a need in the art for polymeric substrates having enhanced affinity for viruses to allow efficient removal from a biological sample. There is further need in the art for ligand functionalized membranes that overcome limitations in diffusion and binding, and that may be operated at high throughput and at lower pressure drops.

SUMMARY OF THE INVENTION

The present invention is directed to ligand functionalized substrates, preferably porous substrates, and methods of making the same. More specifically, the functionalized substrates include a base substrate, preferably a porous base substrate, which has been modified to provide grafted ligand groups having the requisite specific binding capacity for binding charged biomaterials, such as viruses. The ligand functionalized substrate may be described as the grafted reaction product of a substrate and a ligand compound of Formulas I or II:

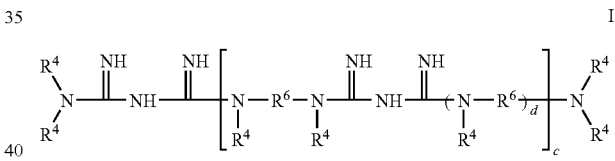

wherein each $R^4$ is individually H, alkyl or aryl,
each $R^6$ is individually alkylene or arylene,
c may be zero or an integer from 1 to 500, and
d is zero or 1, with the proviso that when d is zero, then c is 1 to 500;
or

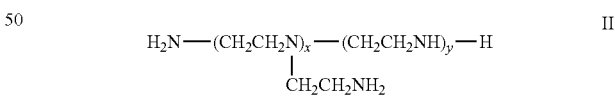

wherein x may be zero, y is at least 1, and x+y is 2 to 2000.

Methods of making a ligand functionalized substrate are provided. The methods may comprise:

providing a substrate, preferably a porous substrate, that may be a thermoplastic or a polysaccharide polymer;

grafting an electrophilic functional group to the surface of the substrate to produce a substrate having grafted electrophilic functional groups extending from the surface(s) thereof; and reacting the grafted electrophilic groups with a ligand compound of Formulas I and/or II to produce a substrate having grafted ligand groups extending from the surface(s) of the substrate.

In some embodiments, the substrate polymer has surface functional groups to which a grafting compound may be attached. Grafting compounds have a first functional group that is reactive toward the surface functional groups of the substrate polymer, and a second electrophilic functional group that is reactive to an amine (or imine) of the ligand compounds. For example, polysaccharide substrates have hydroxyl groups which may be reacted with a grafting compound by addition, condensation or displacement reactions with a grafting compound to provide a grafted, reactive electrophilic functional group for subsequent reaction with the ligand compound.

In other embodiments, the substrate polymer has no such surface functional groups; polymers such as polypropylene may either be exposed to plasma discharge to provide surface hydroxyl groups that may be used to react with the grafting compound. Alternatively, polymers such as polypropylene may be grafted with ethylenically unsaturated grafting monomers having an ethylenically unsaturated group for ionizing radiation-initiated grafting to provide free radical to the polymer surface and a second reactive electrophilic functional group for subsequent reaction with the ligand compounds.

An article is provided comprising a substrate, preferably a porous substrate having interstitial and outer surfaces, and grafted biguanide ligand groups extending from the surfaces thereof, the ligand groups derived from ligand compound of Formula I, the grafted biguanide ligand groups corresponding to one or more of Formulas III to VIII, where $R^2$ and a are as previously defined. For illustration, only biguanide compounds are shown. Similar linkages are formed with bis-biguanide and poly(biguanide) compounds.

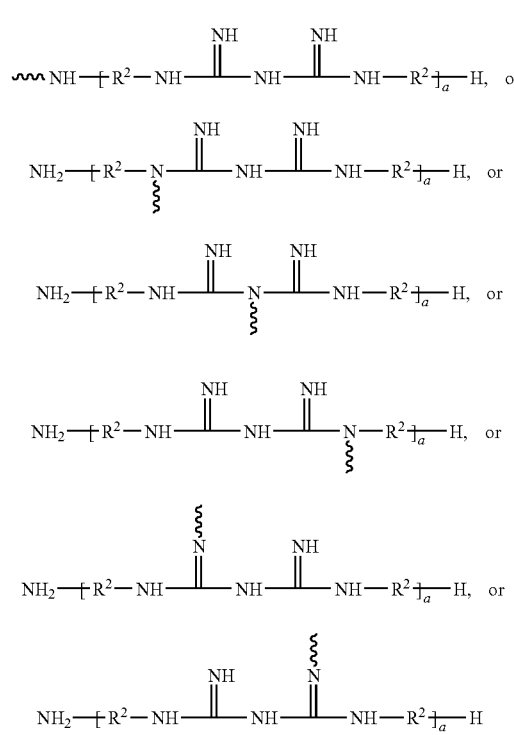

The preparation of biguanide, bis-biguanide and poly (biguanide) compounds of Formula I are known in the art. Reference may be made to F. H. S. Curd and F. L. Rose, *J. Chem. Soc.*, 1946, 729-737, O'Malley et al., J. Appl. Microbiol. 103: 1158, 2007 and East et al., Polymer, 38:3973, 1997 which describe the synthesis of many biguanides. The synthesis of bis-biguanides is discussed by F. L. Rose and G. Swain, *J. Chem. Soc.*, 1956, 4422-4425. It will be understood that the preparation of biguanides with an amine and dicyanoamine may yield a complex mixture of products which includes those of Formula I. In particular, the biguanides may have terminal or pendant cyano groups.

Alternately, an article is provided comprising a substrate, preferably a porous substrate having interstitial and outer surfaces, and grafted ligand groups extending from the surfaces thereof, the ligand groups derived from a ligand compound of Formula II, the grafted ligand groups corresponding to one or more of Formulas IX to XII, where x and y are as previously defined.

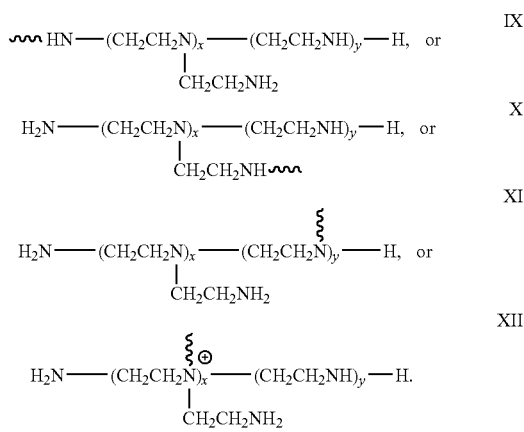

Alternatively, with respect to the ligand compound of Formula II, the grafted ligand group may be depicted as having repeat units of the formulas:

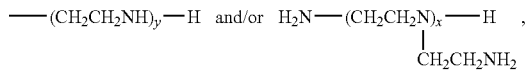

where each of x and y may be zero or a non-zero value, and x and/or y is at least 2. The indicated repeat units are grafted to the substrate surface through one or more of the nitrogen atoms, as depicted supra. It will be understood that the preparation of polyalkyleneimines yield a complex mixture of products that may include both linear and branched polymers, and which may be random, block or alternating copolymers of the units supra, or more complex branched mixtures.

With respect to the above Formulas III to XII, the "~" represents a covalent bond or an organic linking group interposed between the ligand group and the surface of the base substrate. The linking group represents the residue of the grafting monomer or grafting compound. The article may further comprise grafted ionic or hydrophilic groups extending from the surfaces of the substrate.

These and other features and advantages of the present invention will become apparent after a review of the following detailed description of the disclosed embodiments and the appended claims.

DETAILED DESCRIPTION OF THE INVENTION

In the article and methods of this disclosure, ligand-functionalized articles are provided by a process of functionalizing of the substrate by grafting and subsequent reaction of the graft-functionalized substrate with a ligand compound of Formulas I and II and optionally an ionic or hydrophilic compound or an ionic or hydrophilic grafting monomer. Compared to the base substrate before surface modification, the ligand functionalized substrate typically has enhanced binding selectivity for charged biological materials such as host cell proteins, DNA, RNA and viruses. The binding selectivity for such biomaterials allows positively charged materials, such as antibodies to be passed, as they are not bound to the ligand functional groups. The ligand functionalized substrate allows the selective capture or binding of target biomaterials by the ionic interaction between target biomolecules and the ligand groups, while other materials, lacking the specific binding interactions for the ligand groups are passed.

The ligand functionalized substrate comprises a number of components including, but not limited to, (1) a base substrate, and (2) the reaction product of (a) a grafted reactive electrophilic functional group extending from the surfaces of the base substrate, with (b) one or more ligand compounds of Formulas I or II. The reaction product corresponds to one or more of Formulas III to XII. Preferably the base substrate is a porous base substrate having interstitial and outer surfaces. The substrate may be a thermoplastic polymer or a polysaccharide polymer.

In one embodiment, the substrate comprises a polysaccharide. The term "polysaccharide" includes compounds made up of many, hundreds or thousands, of monosaccharide units per molecule connected by glycoside linkages. Their molecular weights are normally higher than about 5,000 and can range up to millions of daltons. They are normally naturally occurring polymers, such as, for example, starch, glycogen, cellulose, gum arabic, agar, and chitin. The polysaccharide should have one or more reactive hydroxy groups. It may be straight or branched chain. The most useful of the polysaccharides for the purposes of this invention is cellulose.

The polysaccharide is preferably fully unprotected and carries all of its hydroxy groups in the free state. Some blocking of the hydroxy groups is possible, as for example, by acylation or aminoacylation. Extensive blocking of the hydroxy groups of the polysaccharide, however, is undesirable since the polysaccharide thereby loses its hydrophilic character, which provides appropriate chemically compatible interaction with biomolecules. If the polysaccharide becomes too hydrophobic, negative interactions with such molecules as proteins lead to possible nonspecific bonding and denaturation phenomena. Also, if the masking of the polysaccharide hydroxy groups is too extensive, the reactivity of the polymer is greatly diminished. For all of these reasons, it is preferred to retain substantially all hydroxy groups in the free state. The polysaccharide is chemically activated by the reactive functional groups described herein.

Cellulose is the preferred polysaccharide. By "cellulose" it is intended to mean any of the convenient and commercially available forms of cellulose such as wood pulp, cotton, hemp, ramie, or regenerated forms such as rayon. There exists no criticality as to the selection of a suitable form of cellulose. Cellulose is a naturally occurring polysaccharide consisting of beta 1,4 linked glucose units. In the native state, adjacent cellulose chains are extensively hydrogen-bonded, forming microcrystalline regions. These regions are interspersed by amorphous regions with less hydrogen bonding. Limited acid hydrolysis results in preferential loss of the amorphous regions and gives so-called microcrystalline cellulose. The cellulose useful in the present invention is either cellulose in the native state or in the microcrystalline state. Also, cellulose derived from cotton linter may be preferable to that derived from wood pulp, as the latter contains lignin.

Chemical reactions to attach the ligand groups to the polysaccharide material normally proceed with difficulty in crystalline regions but take place more readily in amorphous regions. For example, the substitution of functional groups into cellulose has a disruptive effect on the structure thereof. If carried out to completion, the cellulose matrix would be destroyed and ultimately water-soluble polymers would be formed. Typical examples of this phenomenon are the hydroxyethyl cellulose and cellulose gums of the prior art, which become the commonly used adhesives and binders after dissolving in water.

Each saccharide unit in a polysaccharide molecule may have three or more reactive hydroxy groups. All or a portion of the hydroxyl groups may be substituted with the ligand group. The product from such reaction, however, would have a degree of substitution of three or more, which in case of ion-exchange materials, may denature the polymer. Even at lower levels of substitution below those at which total water solubility occurs, such polysaccharide derivatives may become unsuitable as chromatographic supports. Therefore, substitution of the polysaccharide is desirably restricted to the more reactive centers of the amorphous regions and is seldom carried out beyond the level of about 1 mEq/gm of dry weight of the saccharide polymer. At this level of substitution, the native configuration of the polysaccharide structure is only slightly modified, and the low-density, non-uniform exchange sites are readily accessible to large biomolecules.

The final structure of a molecular support of the invention thus comprises a polysaccharide chain covalently graft-modified at a multiplicity of sites along such chain with the ligand groups.

The substrate may be in any form such as films or sheets. Preferably the substrate (e.g., the polysaccharide substrate) is porous, which include, but are not limited to, porous membranes, porous nonwoven webs, and porous fibers. The substrate could be made by a number of methods, including casting from solvent, wet laid fibers, or dry laid fibers.

In another embodiment, the substrate may be formed from any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

In some embodiments, the thermoplastic polymer may be surface treated, such as by plasma discharge, to provide suitable functionality to the surface of the substrate. Surface treatment provides functional groups such as hydroxyl groups, enabling grafting with a grafting compound and subsequent reaction with a ligand compound. One such useful plasma treatment is described in U.S. Pat. No. 7,125,603 (David et al.).

Suitable polyolefins include, but are not limited to, poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly(iminoadipolyiminohexamethylene), poly(iminoadipolyiminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

A preferred substrate is a porous substrate that is a hydrophilic microporous membrane such as a thermally-induced phase separation (TIPS) membrane. TIPS membranes are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching. Microporous membranes are further disclosed in U.S. Pat. No. 4,529,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes comprise poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. For some applications, a TIPS membrane comprising PVDF is particularly desirable. TIPS membranes comprising PVDF are further described in U.S. Pat. No. 7,338,692 (Smith et al.).

The base substrate may be in any form such as films or sheets. Preferably the base substrate is porous. Suitable porous base substrates include, but are not limited to, porous membranes, porous nonwoven webs, and porous fibers.

In many embodiments, the base substrate has an average pore size that is typically greater than about 0.2 micrometers in order to minimize size exclusion separations, minimize diffusion constraints and maximize surface area and separation based on binding of a target molecule. Generally, the pore size is in the range of 0.1 to 10 micrometers, preferably 0.5 to 3 micrometers and most preferably 0.8 to 2 micrometers when used for binding of viruses. The efficiency of binding other target molecules may confer different optimal ranges.

The functionalized substrate, whether thermoplastic or polysaccharide, has grafted groups attached to the surfaces of the base substrate which includes a) at least one ligand group, with b) optionally one or more hydrophilic groups and/or ionic groups.

The substrate, having a reactive group thereon is further reacted with a ligand compound to provide the ligand groups grafted to the surface(s) of the substrate.

In another embodiment, the ligand compound is of the formula:

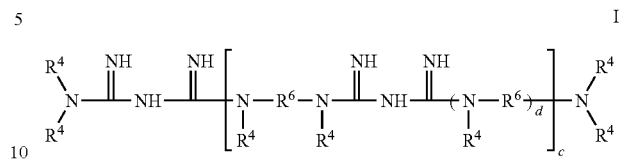

wherein each $R^4$ is individually H, alkyl or aryl,
each $R^6$ is individually alkylene or arylene,
c may be zero or an integer from 1 to 500, preferably at least 5, more preferably 5-500; and
d is zero or 1, with the proviso that when d is zero, then c is 1 to 500;
or

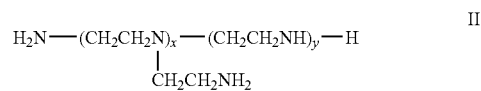

wherein x and y are at least 1, and x+y is 2 to 2000. When grafted to the surface of the substrate, the grafted ligand groups may be represented by the Formulae III to XII (supra).

The above-described ligand functionalized substrates may be prepared using a combination of process steps. In some embodiments, the method comprises:

providing a substrate, preferably a porous substrate that may be a thermoplastic or a polysaccharide polymer, grafting an electrophilic functional group to the surface of the substrate, with a grafting compound or grafting monomer, to produce a substrate having grafted electrophilic functional groups extending from the surface(s) thereof; and reacting the grafted electrophilic functional group with a ligand compound of Formula I or II to produce a substrate having grafted ligand groups extending from the surface(s) of the substrate as depicted in Formulas III to XII.

In one embodiment, the method comprises:
1) providing a base polysaccharide substrate, preferably a porous base substrate, having interstitial and outer surfaces;
2) grafting the base polysaccharide substrate by contacting with a grafting compound having a first functional group reactive with the hydroxyl groups of the polysaccharide substrate and second functional group to produce a surface modified polysaccharide substrate having grafted second functional groups, said second grafted functional groups being either electrophilic functional groups, or groups that may be converted to electrophilic functional groups; and
3) subsequently contacting the surface modified polysaccharide substrate having grafted electrophilic functional groups with a ligand compound of Formulas I and/or II.

In one embodiment, the grafting compound of step two has a second electrophilic functional group that is reactive with the amine (or imine) groups of the ligand compound. In a second embodiment, the grafting compound has a functional group that may be converted to an electrophilic functional group reactive with the amine group of the ligand compound. For example, the polysaccharide substrate may first be reacted with allyl glycidyl ether, wherein the epoxy group is reactive toward the hydroxy groups of the polysaccharide polymer. The resultant grafted allyl groups however, are not reactive toward the amine group of the ligand compound, but may be reacted with N-bromosuccinimide or bromine water to produce a terminal bromo group which is electrophilic and reactive (by nucleophilic displacement) with the amine (or imine) groups of the ligand compounds of Formulas I and II.

In one embodiment, the grafting compound has a group capable of reacting with a hydroxy group of polysaccharide with the formation of a covalent bond. The chemical groups are capable of reacting with hydroxy groups at temperatures up to those at which the polysaccharide begins to decompose or depolymerize, e.g., 0° to 120° C., in aqueous solution and thereby form covalent bonds with the hydroxy groups. Since water may be present in considerable excess with respect to the hydroxy groups of the polysaccharide, chemical groups which react spontaneously with water, such as, for example, isocyanate groups, are less suitable.

Hydroxy reactive groups of the grafting compound may be activated carboxy groups such as are known from peptide chemistry or O-alkylating agents, such as alkyl halide or epoxide groups. Representatives of the O-alkylating comonomers are acrylic and methacrylic anhydrides, acrylolyl or methacrylol N-hydroxy succinimides, $\Omega$-haloalkyl esters of acrylic or methacrylic acid in which the alkyl group in general contains two to six carbon atoms, allyl halides, chloromethylstyrene, chloroacetoxy allyl ether, and compounds having a glycidyl group. The latter are ethers or esters formed between a glycidyl alcohol and an unsaturated alcohol or unsaturated carboxylic acid, respectively. The glycidyl alcohols are aliphatic and cycloaliphatic alcohols and ether alcohols having from 3 to 18 carbon atoms which are esterified with an $\alpha,\beta$-unsaturated carboxylic acid, preferably acrylic or methacrylic acid, or are etherified with an olefinically or acetylenically unsaturated alcohol. Typical compounds are glycidyl acrylate and methacrylate; 4,5-epoxy-pentylacrylate; 4-(2,3-epoxy-propyl)-N-butyl-methacrylate; 9,10-epoxy-stearylacrylate; 4-(2,3-epoxypropyl)-cyclohexyl methylacrylate; ethylene glycol-monoglycidyl etheracrylate; and allyl glycidyl ether.

Other useful grafting compounds that may be used to graft to the surface of the polysaccharide substrate include cyanuric chloride, N-hydroxysuccinimide esters, the multifunctional compounds with terminal acyl sulfonamide groups as described in U.S. Pat. No. 7,402,678 (Benson et al.), the halo phosphonitrile compounds described in U.S. 2005/0142296A (Lakshmi et al.), triazine compounds as described in U.S. 2007/0065490 (Schaberg et al.), the N-sulfonyldicarboximide compounds described in U.S. Pat. No. 7,361,767 and U.S. Pat. No. 7,169,933 (Benson et al.)

In some embodiments, the polysaccharide substrate further comprises grafted ionic groups such as quaternary ammonium groups. Such groups may be grafted by contacting the polysaccharide substrate with epichlorohydrin and base, react with a tertiary amine, or a secondary amine followed by alkylation. Alternatively, quaternary ammonium groups may be grafted to the surface of the substrate by reaction with glycidyltrimethylammonium chloride. In some embodiments, the polysaccharide substrate further comprises grafted hydrophilic groups, such as poly(ethylene oxide) groups, which may be grafted by reaction of the substrate with a compound such as poly(ethylene oxide) mono- or diacid.

Other polymers, lacking functional groups such as the hydroxyl groups of polysaccharides, are advantageously functionalized with an ionizing radiation grafting technique. In this embodiment, thermoplastic polymers, such as polypropylene or polyvinylidene fluoride (PVDF), are first grafted with a grafting monomer, and subsequently reacted with the ligand compound of Formulas I or II. The grafting monomers have an ethylenically unsaturated group which, when exposed to ionizing radiation in the presence of the substrate leads to a radical-initiated covalent attachment to the surface of the substrate. As result, the substrate is functionalized with the grafting monomer.

The functionalized substrate has grafted species, the grafting monomer, attached to the surfaces of the base substrate. The grafting of grafting monomers to the surface of the porous base substrate results in the attachment of a functional group that is reactive with an amine (or imine) group of the ligand compounds or Formulas I and II. This amine group may be present on the terminus of the ligand compound, such as a primary amine or may be present in the interior of the ligand compound, such as a secondary amine, or as a primary amine on a branching moiety. The grafting monomers have both (a) a free-radically polymerizable group and (b) at least one additional second functional group thereon. The additional second functional group of the grafting monomer may be an electrophilic group, or another functional group that may be converted to an electrophilic group.

The free-radically polymerizable group is typically an ethylenically unsaturated group such as a (meth)acryloyl group or a vinyl group. The free-radically polymerizable group typically can react with the surface of the porous base substrate when exposed to an electron beam or other ionizing radiation. That is, reaction of the free-radically polymerizable groups of the grafting monomers with the surface of the porous base substrate in the presence of the electron beam results in the formation of grafted species attached to the porous base substrate. One or more grafting monomers may be grafted onto interstitial and outer surfaces of the porous base substrate.

In addition to having a free-radically polymerizable group, suitable grafting monomers have an additional functional group such as an epoxy group, an azlactone group, an isocyanato group, a halo group, that is reactive toward the amine group of the ligand compound, or can be further activated to be reactive toward the amine group of the ligand compounds such as an allyl group. That is, after the grafting monomer has been attached to the porous base substrate through a reaction involving the free-radically polymerizable group, the additional functional group of the resulting grafted species can be reacted further with the ligand compound.

In addition, optional grafting monomers may have functional groups used to provide further reactivity, or binding specificity for particular analytes (or which would retard binding of other analytes) such as an ionic group, a second ethylenically unsaturated group, an alkylene oxide group, or a hydrophobic group. In these instances, the additional functional group can impart a desired surface property to the functionalized substrate such as affinity for a particular type of compound. If the grafted species contains an ionic group, the functionalized substrate will often have an affinity for compounds having an opposite charge. That is, compounds with negatively charged groups can be attracted to a functionalized substrate having grafted species with a cationic group and compounds with positively charged groups can be attracted to a functionalized substrate having grafted species with an anionic group. Further, the grafted species can impart a hydrophilic surface to the functionalized substrate that includes a porous base substrate having a hydrophobic surface prior to surface modification with the grafted species. That is, the grafted species contain an alkylene oxide group can impart a hydrophilic character to the resulting functionalized substrate.

Some grafting monomers have a) a first ethylenically unsaturated group for grafting to the surface of the substrate and b) an additional functional group that is an epoxy group. Suitable grafting monomers within this class include, but are not limited to, glycidyl (meth)acrylates. This class of grafting monomers can provide a functionalized substrate having at least one epoxy group available for further reactivity. The epoxy group can react with the ligand compound, which results in the opening of the epoxy ring and the formation of a linkage group that functions to attach the ligand compound to the porous base substrate. The linkage group formed by ring-opening of the epoxy group often contains the group —C(OH)HCH$_2$NH— when the epoxy is reacted with a primary amino group of the ligand compound. The epoxy group can react with other reactants such as another nucleophilic compound to impart a desired surface property to the base substrate (e.g., binding specificity for a particular compound or functional group having different reactivity).

Other grafting monomers have a (a) free-radically polymerizable group that is an ethylenically unsaturated group and (b) an additional functional group that is an azlactone group or a precursor to an azlactone group. Suitable grafting monomers include, but are not limited to, vinyl azlactone such as 2-vinyl-4,4-dimethylazlactone and N-acryloyl-2-methylalanine. This class of grafting monomers can provide a functionalized substrate having at least one azlactone group (or a precursor to an azlactone group) available for further reactivity with the ligand compound. The azlactone group can react with other reactants such as another monomer or with a nucleophilic compound to impart a desired surface property to the porous base substrate (e.g., binding specificity for a particular compound or functional group having different reactivity). The reaction of the azlactone group with a ligand compound, for example, results in the opening of the azlactone ring and the formation of a linkage group that functions to attach the nucleophilic compound to the porous base substrate. The linkage group formed by ring-opening of the azlactone group often contains the group CH$_2$=CH—(CO)NHC(R$^3$)$_2$ (CO)— where R$^3$ is an alkyl such as methyl.

In some embodiments, the azlactone groups can be reacted with a monofunctional amine such allyl amine wherein the amine group can react by a ring opening reaction with the azlactone group and result in the formation of a linkage containing the group CH$_2$=CH—(CO)NHC(R$^3$)$_2$(CO)NH—CH$_2$—CH=CH$_2$. The grafted allyl group may then be converted to an electrophilic functional group for further reaction with the ligand compounds of Formulas I and II. For example, the terminal allyl group may be brominated, by a suitable brominating agent such as N-bromosuccinimide to produce a terminal electrophilic bromide, which may then be reacted with the nucleophilic nitrogen atoms of the ligand compounds of Formulas I and II to produce the pendant ligand groups of Formulas III to XII.

In some embodiments, the azlactone groups can be reacted with a multifunctional amine such as a diamine having two primary amino groups or a triamine having three primary amino groups. One of the amino groups can react by a ring opening reaction with the azlactone group and result in the formation of a linkage containing the group —(CO) NHCR$^3$$_2$(CO)— between the nucleophilic compound and the base substrate. The second amino group or second and third amino groups can import a hydrophilic character to the functionalized substrate. In some examples, the multifunctional amine is a polyalkylene glycol diamine or a polyalkylene glycol triamine and reaction with an azlactone group results in the attachment of a grafted species having a polyalkylene glycol group (i.e., polyalkylene oxide group). The polyalkylene glycol group as well as any terminal primary amino group tends to impart a hydrophilic character to the functionalized substrate.

Other grafting monomers have a (a) free-radically polymerizable group that is an ethylenically unsaturated group and (b) an additional functional group that is an isocyanato group. Suitable grafting monomers include, but are not limited to an isocyanatoalkyl (meth)acrylate such as 2-isocyanatoethyl methacrylate and 2-isocyanatoethyl acrylate. This class of grafting monomers can provide a functionalized substrate having at least one isocyanato group available for reactivity. The isocyanato group can react with other reactants such as the ligand compounds or with a nucleophilic compound to impart a desired surface property to the functionalized substrate (e.g., affinity for a particular compound or functional group having different reactivity). The reaction of an isocyanato group with an amine group of the ligand compounds can result in the formation of a urea linkage.

Yet other optional grafting monomers have a (a) free-radically polymerizable group that is an ethylenically unsaturated group and (b) an additional ionic functional group. The ionic group can have a positive charge, a negative charge, or a combination thereof. With some suitable ionic monomers, the ionic group can be neutral or charged depending on the pH conditions. This class of monomers is typically used to impart a desired surface binding specificity for one or more oppositely charged compounds or to decrease the affinity for one or more similarly charged compounds.

Some exemplary ionic grafting monomers having a negative charge include, but are not limited to, N-acrylamidomethanesulfonic acid, 2-acrylamidoethanesulfonic acid, 2-acrylamido-2-methyl-1-propanesulfonic acid, and 2-methacrylamido-2-methyl-1-propanesulfonic acid. Salts of these acidic monomers can also be used. Counter ions for the salts can be, for example, ammonium ions, potassium ions, lithium ions, or sodium ions.

Other suitable ionic grafting monomers having a negative charge include sulfonic acids such as vinylsulfonic acid and 4-styrenesulfonic acid; (meth)acrylamidophosphonic acids such as (meth)acrylamidoalkylphosphonic acids (e.g., 2-acrylamidoethylphosphonic acid and 3-methacrylamidopropylphosphonic acid); acrylic acid and methacrylic acid; and carboxyalkyl(meth)acrylates such as 2-carboxyethylacrylate, 2-carboxyethylmethacrylate, 3-carboxypropylacrylate, and 3-carboxypropylmethacrylate. Still other suitable acidic monomers include (meth)acryloylamino acids, such as those described in U.S. Pat. No. 4,157,418 (Heilmann), incorporated herein by reference. Exemplary (meth) acryloylamino acids include, but are not limited to, N-acryloylglycine, N-acryloylaspartic acid, N-acryloyl-.beta.-alanine, and 2-acrylamidoglycolic acid. Salts of any of these acidic monomers can also be used.

Some exemplary ionic grafting monomers that are capable of providing a positive charge are amino (meth) acrylates or amino (meth)acrylamides or quaternary ammonium salts thereof. The counter ions of the quaternary ammonium salts are often halides, sulfates, phosphates, nitrates, and the like. Exemplary amino (meth)acrylates include N,N-dialkylaminoalkyl(meth)acrylates such as, for example, N,N-dimethylaminoethylmethacrylate, N,N-dimethylaminoethylacrylate, N,N-diethylaminoethylmethacylate, N,N-diethylaminoethylacrylate, N,N-dimethylaminopropylmethacrylate, N,N-dimethylaminopropylacrylate, N-tert-butylaminopropylmethacrylate, N-tert-butylaminopropylacrylate and the like. Exemplary amino (meth)acrylamides include N-(3-aminopropyl)methacrylamide, N-(3-aminopropyl)acrylamide, N-[3-(dimethylamino)propyl]methacrylamide, N-(3-imidazolylpropyl)methacrylamide, N-(3-imidazolylpropyl)acrylamide, N-(2-imidazolylethyl)methacrylamide, N-(1,1-dimethyl-3-imidazoylpropyl)methacrylamide, N-(1,1-dimethyl-3-imidazoylpropyl)acrylamide, N-(3-benzoimidazolylpropyl)acrylamide, and N-(3-benzoimidazolylpropyl)methacrylamide.

Exemplary quaternary salts of the ionic monomers include, but are not limited to, (meth)acrylamidoalkyltrimethylammonium salts (e.g., 3-methacrylamidopropyltrimethylammonium chloride and 3-acrylamidopropyltrimethylammonium chloride) and (meth) acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other grafting monomers that can provide positively charged groups to the surface of the substrate include the dialkylaminoalkylamine adducts of alkenylazlactones (e.g., 2-(diethylamino)ethylamine, (2-aminoethyl)trimethylammonium chloride, and 3-(dimethylamino)propylamine adducts of vinyldimethylazlactone) and diallylamine monomers (e.g., diallylammonium chloride and diallyldimethylammonium chloride).

Functionalized substrates of the present invention may be prepared using one of the above-described grafting monomers or a mixture of two or more of the above-described grafting monomers to provide a functional group for further reaction with the ligand compounds and/or alter the surface properties of a base substrate. When two or more of the above-described grafting monomers are used to alter the surface properties of a porous base substrate, the monomers may be grafted onto the porous base substrate in a single reaction step (i.e., the two or more grafting monomers are all present upon exposure to an electron beam) or in sequential reaction steps (i.e., a first grafting monomer is present upon a first exposure to an electron beam and a second grafting monomer is present upon a second exposure to the electron beam.

It will be understood that the grafting monomers may polymerize on the surface of the substrate to yield a grafted polymer having pendant electrophilic functional groups. These pendant electrophilic functional groups may then be further reacted with the ligand monomers of Formulas I and II to yield a grafted polymer having pendant ligand groups. Such a polymer may be depicted as Substrate~$(M_{ligand})_m$, where $M_{ligand}$ represent a polymerized grafted monomer having pendant ligand groups, and m is at least two. Such polymers may further comprise other optional grafting monomers.

For radiation grafting, one embodiment of the method comprises:
1) providing a base substrate, preferably a porous base substrate having interstitial and outer surfaces;
2) imbibing the porous substrate with a first solution comprising (a) one or more grafting monomers having at least one acryloyl group and at least one second electrophilic functional group, or a second functional group that may be converted to an electrophilic functional group;
3) exposing the imbibed porous base substrate to ionizing radiation, preferably e-beam or gamma radiation, so as to form a first functionalized substrate comprising a base substrate having grafted electrophilic functional groups (from the grafting monomer) attached to the surface(s) thereof; and
4) contacting the substrate having grafted electrophilic functional groups to the ligand compounds of Formula I or II to produce a substrate having grafted ligand groups attached to the surface(s) thereof, as illustrated by Formulas III to XII.

In another embodiment, the imbibing step 2 may comprise imbibing the substrate with a grafting monomer having an electrophilic functional group. This electrophilic functional group may be further functionalized with a compound having a nucleophilic functional group and a second, non-electrophilic group that may be converted to an electrophilic group. For example, a grafting monomer such as vinyl dimethylazlactone may be grafted to the surface of the substrate. This in turn may be reacted with a nucleophilic compound such as allyl amine, the allyl group of which is not reactive with the ligand compounds, by may be converted to an electrophilic group, such as a bromo group by reaction with N-bromosuccinimide or bromine water.

In some embodiments, the imbibing solution may comprise optional grafting monomers that may impart grafted ionic or hydrophilic groups to the surface of the substrate. For example, optional grafting monomers may comprise hydrophilic mono- and diacrylates of poly(ethylene oxide).

In another embodiment, the method comprises:
1) providing a porous base substrate having interstitial and outer surfaces;
2) imbibing the porous base substrate with a first solution to form an imbibed porous base substrate, the first solution comprising (a) at least one grafting monomer having an acrylate group and a photoinitiator group and (b) one or more monomers having at least one acrylate group and at least one additional ethylenically unsaturated, free-radically polymerizable group; and optionally (c) one or more additional monomers having at least one free-radically polymerizable group and an electrophilic group;
3) exposing the imbibed porous base substrate to a controlled amount of electron beam radiation so as to form a first functionalized substrate comprising grafted photoinitiator groups attached to the surfaces of the porous base substrate, and
4) optionally imbibing the substrate comprising grafted photoinitiator groups with an imbibing solution comprising a grafting monomer having an electrophilic group;
5) exposing the porous base substrate comprising grafted photoinitiator groups to a controlled amount of UV radiation to polymerize or crosslink the remaining ethylenically unsaturated, free-radically polymerizable groups and incorporating the grafting monomer having the electrophilic group, and
6) contacting the substrate having grafted electrophilic groups to the ligand compounds of Formulas I and/or II, wherein at least one of steps 2 or 4 contain a grafting monomer having an electrophilic group.

Further reference regarding this method may be found in Assignee's copending application U.S. 2009/0098359, incorporated herein by reference in its entirety.

The ionizing radiation grafting methods involve the irradiation of substrate surfaces with ionizing radiation to prepare free radical reaction sites on such surfaces upon which the monomers are grafted. "Ionizing radiation" means radiation of a sufficient dosage and energy to cause the formation of free radical reaction sites on the surface(s) of the base substrate. Ionizing radiation may include beta, gamma, electron-beam, x-ray and other forms of electromagnetic radiation. In some instances, corona radiation can be sufficiently high energy radiation. The radiation is sufficiently high energy, that when absorbed by the surfaces of the base substrate, sufficient energy is transferred to that support to result in the cleavage of chemical bonds in that support and the resultant formation of a free radical site on the support.

High energy radiation dosages are measured in kilograys (kGys). Doses can be administered in a single dose of the desired level or in multiple doses which accumulate to the desired level. Dosages can range cumulatively from about 1 kGys to about 100 kGys depending on the source of radiation. Generally, e-beam dosage is higher than gamma. Preferably, the cumulative dosage exceeds 30 kGys for substrates resistant to radiation damage when using e-beam. Doses in the range of 3 to 7 kGys are usually acceptable for all polymers when using gamma radiation.

Electron beam and gamma radiation are preferred for this method of grafting due to the ready-availability of commercial sources. Electron beam generators are commercially available from a variety of sources, including the ESI "ELECTROCURE" EB SYSTEM from Energy Sciences, Inc. (Wilmington, Mass.), and the BROADBEAM EB PROCESSOR from PCT Engineered Systems, LLC (Davenport, Iowa). Sources of gamma irradiation are commercially available from MDS Nordion using a cobalt-60 high-energy source. For any given piece of equipment and irradiation sample location, the dosage delivered can be measured in accordance with ASTM E-1275 entitled "Practice for Use of a Radiochromic Film Dosimetry System." By altering the source strength and the area spread various dose rates can be obtained.

Further details of the radiation grafting methods may be found in Assignee's U.S. 2007/0154703 (Waller et al.), incorporated herein by reference in its entirety.

In one embodiment, the method provides an article having a grafted, ligand functionalized surface, comprising the reaction product of a grafted functional group and one or more ligand monomers. The method of making a ligand functionalized substrate alters the original nature of the porous base substrate, as the grafted species include a ligand group. The present invention enables the formation of ligand functionalized substrates having many of the advantages of a base substrate (e.g., mechanical and thermal stability, porosity), but with enhanced binding specificity for biomolecules such as viruses, resulting from the monomers and steps used to form a given functionalized substrate. The present invention reduces or eliminates many of the known problems associated with porous base substrates formed from hydrophilic polymers including, but not limited to, hygroexpansive issues; brittleness without humidification problems; mechanical strength weakness; and poor solvent, caustic and/or acidic resistance.

In one embodiment, the grafting monomer having optional hydrophilic groups can be used to impart a hydrophilic character to a hydrophobic base substrate, such as a PVDF substrate. These grafting monomers may have a hydrophilic poly(alkylene oxide) group.

Alternatively, optional grafting monomers may optionally contain an ionic group. In these instances, hydrophilicity is imparted using a monomer, which may contain a grafting acrylate group or a non-acrylate polymerizable group, and a hydrophilic group, such as a quaternary ammonium group. Such ionic groups may further impart enhanced selectivity to the functionalized substrate by repelling biological species having a like charge as the ionic group, at the appropriate pH.

The ligand-functionalized porous substrates are particularly suited as filter media, for the selective binding and removal of viruses, such as endogenous or adventitious viruses, from biological samples. As the ligand is grafted to the base substrate (either directly or indirectly), the ligand functionalized substrate is durable. The present disclosure then further provides a method for the removal of viruses from a virus-containing sample, such as a biological sample comprising contacting a sample with the ligand functionalized substrate as described herein.

The sample is contacted with the virus-capture membrane for a time sufficient to yield a log-reduction value (LRV) of at least 1.0 for neutral viruses disposed in the solution when the solution comprises from 0 to about 50 mM salt, preferably to yield a log-reduction value (LRV) of at least 1.0 for neutral viruses disposed in the solution when the solution comprises from 0 to about 100 mM salt, and more preferably still to yield a log-reduction value (LRV) of at least 1.0 for neutral viruses disposed in the solution when the solution comprises from 0 to about 150 mM salt. It is still more preferred that the solution is contacted with the virus-capture membrane for a time sufficient to yield a log-reduction value (LRV) of at least 5.0 for neutral viruses disposed in the solution when the solution comprises from 0 to about 50 mM salt, preferably to yield a log-reduction value (LRV) of at least 5.0 for neutral viruses disposed in the solution when the solution comprises from 0 to about 100 mM salt, and more preferably still to yield a log-reduction value (LRV) of at least 5.0 for neutral viruses disposed in the solution when the solution comprises from 0 to about 150 mM salt. The term neutral virus is used to denote any virus that has an isoelectric point (pI) around 7, or optionally, nominally between 6 and 8. Alternatively, the term "near-neutral" may be used. The sample solution pH is such that the virus is negatively charged.

This importance of viral clearance in the presence of salt, known as "salt tolerance" is that many process solutions used in biopharmaceutical manufacture have conductivities in the range of 15-30 mS/cm. Salt tolerance is measured in comparison to the conventional Q ligand (AETMA, 2-aminoethyltrimethylammonium chloride), which rapidly loses capacity for some viruses (e.g., $\phi$X174) at conductivities three- to six-fold less than the target range, e.g. dropping viral clearance from a six log-reduction value (LRV) to a one log-reduction value (LRV) in going from 0 to 50 mM NaCl. Viruses such as $\phi$X174 and PM2 have pIs close to 7, (pI for $\phi$X174: 6.6; for PM2: 7.3; for poliovirus type 1: 7.5 (Brunhilde strain) and are neutral or near-neutral.

In many embodiments, the substrate may be functionalized so that other proteins are excluded or repelled from the ligand functionalized substrate, while viruses and other negatively charged species such as host cell proteins, DNA, etc. bind to the ligand functional group. In addition, as previously described, the substrate may be directly or indirectly grafted with one or more ionic monomers. In particular, the porous substrate may comprise grafted ionic groups that are positively charged at the selected pH of the biological sample solution to cause electrostatic charge repulsion of proteins, such as monoclonal antibodies, many of which are charged positive at neutral pH.

Preventing protein binding, such as mAb binding, can be accomplished by increasing the pKa of the ligand, or grafting an additional positively charged functional group, and adjusting the pH of the solution so that the mAb and ligand are both charged positive during loading. This causes electrostatic charge repulsion of the mAb from the ligand and substrate surface. The virus, in contrast, is normally negatively charged and binds to the ligand. Most therapeutic mAbs tend to have pI's between 8 and 10. Thus, mAbs are positively charged at neutral pH, which prevents their binding to substrate surface. Viruses, on the other hand, can have a variety of pI's and many have pI's below 7. Therefore the pH of the sample solution should be maintained below the isoelectric point of the protein of interest (such as a mAb) and above the isoelectric point of the virus.

The ligands and other grafted functional groups herein are selected based on the above criteria and outcomes, i.e., it is salt tolerant and has a high pKa (e.g., >10) causing electrostatic charge repulsion of the mAb. The ligand is immobilized on a porous membrane and the virus-containing fluid flows through the membrane while the virus is trapped by the ligand.

In some embodiments, the grafted article containing the bound virus is disposable. In such embodiments, the binding of the virus to the filter medium is preferably essentially irreversible because there is no need to recover the bound virus. Nonetheless, one can reverse the binding of viruses by increasing the ionic strength of an eluting solution. In contrast, for many instances of protein binding, the binding phenomenon must necessarily be reversible or the desired protein cannot be eluted from the column.

The substrate for viral capture may be any previously described, but is preferably a microporous membrane. The membrane pore size desired is from 0.1 to 10 µm, preferably 0.5 to 3 micrometers and most preferably 0.8 to 2 micrometers. A membrane with a high surface area for the internal pore structure is desired, which typically corresponds to fine pore sizes. However, if the pore size is too small, then the membrane tends to plug with fine particulates present in the sample solution.

If desired, efficiency of viral binding and capture may be improved by using a plurality of stacked, ligand-functionalized porous membranes as a filter element. Thus the present disclosure provides a filter element comprising one or more layers of the porous, ligand functionalized substrate. The individual layers may be the same or different, and may have layers of different porosity, and degree of grafting by the aforementioned grafting monomers. The filter element may further comprise an upstream prefilter layer and downstream support layer. The individual filter elements may be planar or pleated as desired.

Examples of suitable prefilter and support layer materials include any suitable porous membranes of polypropylene, polyester, polyamide, resin-bonded or binder-free fibers (e.g., glass fibers), and other synthetics (woven and non-woven fleece structures); sintered materials such as polyolefins, metals, and ceramics; yarns; special filter papers (e.g., mixtures of fibers, cellulose, polyolefins, and binders); polymer membranes; and others.

In another embodiment, there is provided a filter cartridge including the above-described filter element. In yet another embodiment, there is provided a filter assembly comprising the filter elements and a filter housing. In a further embodiment, this invention relates to a method of viral capture comprising the steps of:

a) providing the filter element comprising one of more layers of the ligand functionalized base substrate of this disclosure, and b) allowing a moving biological solution containing a virus to impinge upon the upstream surface of the filter element for a time sufficient to effect binding of a virus.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Materials

Polyethyleneimine of $M_w$ of about 25,000 was purchased from Alpha Aesar (Ward Hill, Mass.).

Polyhexamethylene biguanide of $M_w$ of about 25,000 was purchased from Arch Chemical (South Plainfield, N.J.).

Regenerated cellulose (RC) discs with a pore size of 0.45 µm, diameter of 25 mm and average thickness of 180 µm were obtained as type 184 from Sartorius, Germany.

PVDF film; a TIPS (thermally-induced phase separation) porous film, 5 mils thick, with a Gurley (air flow) about 4.5 sec/50 cc air, bubble point pore size of about 1.9 microns, 1.4 µm average pore size, 72% porous, and a water flux time of about 10 sec (using 100 ml water, 47 mm Pall Gelman Filter Funnel 4238, at 23 in Hg vacuum). Reference may be made to U.S. Pat. No. 7,338,692 (Smith et al.).

"VAZPIA" refers to 2-propenoylaminoethanoic acid, 2-(4-(2-hydroxy-2-methylpropanoyl)phenoxy)ethyl ester prepared according to Example 1 of U.S. Pat. No. 5,506,279 (Babu et al.).

"PEG 400 diacrylate" diacrylate ester of polyethyleneglycol, molecular weight 400, Aldrich Chemical Co.

Testing of Membranes

Dye Assay

RC membranes derivatized with amine ligands were tested for relative ionic capacity colorimetrically by reaction with a negatively charged orange dye. Tropaeolin O (Acros, Geel, Belgium) was dissolved in 66% (v/v) ethanol to a concentration of 0.5 mg/mL. RC membranes were rinsed in 20% ethanol then incubated in the Tropaeolin O solution for 4 hr at 22° C. The membranes were then removed from the dye solution and washed thoroughly with 20% ethanol to remove unbound dye. A blank RC membrane was used as a control to eliminate the effects of any potential non-specific binding. Finally, the color (a*) of the stained membranes was measured using a ColorQuest colorimeter (HunterLab, Reston, Va.).

Binding of Bovine Serum Albumin:

The membranes were analyzed for binding of proteins by passing solutions of the test analytes through a 6-layer stack of the membranes punched out into 25-mm diameter discs placed in a 25 mm diameter holder attached to an AKTA chromatography system (GE Healthcare, NY). Feed solution was prepared by dissolving bovine serum albumin (BSA) in 50 mM bisTris buffer pH 6 to a concentration of 0.2 mg/mL as determined by absorbance at 280 nm. BSA feed solution was pumped through the membrane adsorber at a flow rate of 5 mL/min until complete breakthrough was observed via absorbance at 280 nm. The dynamic binding capacity of the membrane was evaluated using standard chromatography techniques.

Determination of Viral Capture:

Viral capture was measured using a standard protocol developed at the Food and Drug Administration as described in the PDA Technical Report 41 (TR41), Virus Filtration. The test virus was a bacteriophage φX174. A standard stock solution containing $10^9$ to $10^{12}$ pfu/ml (plaque forming units) in a 10 mM TRIS-HCl buffer at pH 7.5, with NaCl concentration of 0, 50 and 150 mM was prepared. This stock was flowed through the membrane stack as previously described. During loading, 50 mL of challenge solution was pumped through the membrane adsorber at a flow rate of 5 mL/min and flow-through samples were collected every 10 ml. The effluent was collected as 1 ml fractions using a fraction collector. Fractions corresponding to a total throughput of 10 ml, 20 ml, 30 ml, 40 ml and 50 ml through the membranes were taken aside and these were subjected to several decadal dilutions. The virus stock solution was also subjected to a similar dilution series. The diluted fractions were then incubated with E. coli solution and plated onto agar plates along with growth medium comprised of tryptic soy broth. The inverted plates were incubated overnight and the numbers of plaques were counted. The LRV (or log reduction in viral load) was estimated from knowledge of the corresponding dilution factor as well as the initial concentration of the phage and calculated using Eqn (1):

$$LRV = \log_{10}\left(\frac{Titer_{challenge}(pfu/\text{mL})}{Titer_{sample}(pfu/\text{mL})}\right) \quad (1)$$

Example 1 and 2

Part A

Preparation of Substrate Membranes Having Grafted Electrophilic Groups

Grafting of the amine-containing ligands to the RC base membrane was effected by the following method. First, hydroxyl groups on the cellulose substrate were activated by reacting the membranes in a 5% allyl glycidyl ether (as the grafting compound) solution in 30% sodium hydroxide overnight at 22° C. The covalently attached allyl groups were converted to electrophilic bromo groups by bromination using a 10 g/L solution of N-bromosuccinimide for 2 hr.

Part B

Grafting of Functional Groups on Activated Membranes

Grafted bromo groups on the membranes made in Part A were replaced with amine ligands via nucleophilic substitution in which brominated membranes were reacted with amine ligand solution for 2 days at 22° C. to ensure high levels of amine substitution. Ligand solutions were as follows: 10% (w/w) solids in aqueous solution pH 11 for the polyethyleneimine (PEI) and polyhexamethylene biguanidine (PHMB). The BSA capacity, and ΦX174LRV clearance at three salt levels are shown in Table 1.

TABLE 1

| Ligand | BSA Capacity (mg/mL) | ΦX174LRV 0 mM NaCl | 50 mM NaCl | 150 mM NaCl |
|---|---|---|---|---|
| PHMB | 8 ± 1 | 8.8 ± 0.3 | 8.5 ± 0.9 | 7.1 ± 0.1 |
| PEI | 6.1 ± 0.6 | 8.7 ± 0.3 | 6.1 ± 0.4 | 5.8 ± 0.8 |

[1]Values reported as means ± SD, n = 2.

Example 3

The PVDF porous substrate was imbibed with a solution containing 10.0 wt. % PEG 400 diacrylate monomer available from Sartomer Inc. of Exton, as PA SR344™ and 90.0 wt. % methanol. The coated porous substrate was then placed 'wet' between two layers of PET film (first layer and second layer) having a thickness of approximately 100 micrometers. A removable first layer and a removable second layer were each placed on opposite sides of the coated porous substrate with any excess solution and trapped air bubbles squeezed out with a hand held rubber roller. The multilayer structure was conveyed through the electron beam on a carrier web. The multilayer structure was irradiated by electron beam (E-beam) on an ESI CB-300 electron beam with a dose of 20 kGy set at a voltage of 300 keV. Two minutes following irradiation, the hydrophilic functionalized porous substrate was removed from the first and second PET layers. The membrane was soaked in a tray of water that was exchanged three times with DI water to wash the membrane of unreacted monomer and subsequently air dried.

The hydrophilic PVDF porous substrate was coated in a solution containing 10.0% vinyl dimethylazlactone-allyl amine adduct in 20% DI water, and 70% methanol. The solution filled membrane is again subjected to an E-beam dose of 40 kGy set at a voltage of 300 keV, which also grafts this monomer to the surface of the PVDF substrate. After two minutes, the PET sandwich was opened and the grafted PVDF membrane was soaked in a tray of water that was exchanged three times with DI water to wash the membrane of unreacted monomer and subsequently air dried. In addition to the grafted PEG diacrylate, it is believed that the vinyl dimethylazlactone-allyl amine adduct, $CH_2=CH-(CO)NHC(CH_3)_2(CO)NH-CH_2-CH=CH_2$, may be directly grafted to the surface of the substrate; i.e.: substrate-$CH_2CH_2-(CO)NHC(CH_3)_2(CO)NH-CH_2-CH=CH_2$, allowing terminal allyl groups for conversion to electrophilic terminal bromo groups ($-CH_2CH_2CH_2Br$ and/or $CH_2CHBrCH_3$), for subsequent reaction with the ligand compound. Upon grafting, the dimethylazlactone-allyl amine adduct may also polymerize to produce a grafted acrylate polymer having a plurality of pendant $-(CO)NHC(CH_3)_2(CO)NH-CH_2-CH=CH_2$ groups, which may also be converted to terminal bromo groups. The dimethylazlactone-allyl amine adduct may also polymerize with any unreacted acrylate groups from the PEG diacrylate.

A 6 inch×7 inch sample of allyl-functional PVDF membrane was placed in a 500 ml polyethylene bottle and covered with 500 mL of a 10 gram/L solution of N-bromosuccinimide in deionized water. The bottle was sealed and the mixture was allowed to stand at ambient temperature overnight. The excess solution was poured off, and the membrane was washed under a stream of deionized water for 30 minutes. The bottle was then filled with a solution of 10% by weight polyethyleneimine (PEI) in deionized water, the bottle was sealed, and the mixture was tumbled endover-end at ambient temperature for 4 days. The excess solution was decanted, the bottle was filled with deionized water, allowed to stand for 30 minutes, and decanted again. This process was repeated an additional 4 times to thoroughly wash the derivatized membrane, then the membrane was allowed to air dry.

Example 4

The following Example used the general procedures described in Applicant's copending application U.S. 2009/0098359, incorporated herein by reference its' entirety.

The PVDF porous substrate was imbibed with a solution containing 10.0 wt. % PEG 400 diacrylate monomer available from Sartomer Inc. of Exton, Pa. as SR344™ and 90.0 wt. % methanol. The coated porous substrate was then placed 'wet' between two layers of PET film (first layer and second layer) having a thickness of approximately 100 micrometers. A removable first layer and a removable second layer were each placed on opposite sides of the coated porous substrate with any excess solution and trapped air bubbles squeezed out with a hand held rubber roller. The multilayer structure was conveyed through the electron beam on a carrier web. The multilayer structure was irradiated by electron beam (E-beam) on an ESI CB-300 electron beam with a dose of 20 kGy set at a voltage of 300 keV. Two minutes following irradiation, the hydrophilic functionalized porous substrate was removed from the first and second PET layers. The membrane was soaked in a tray of water that was exchanged three times with DI water to wash the membrane of unreacted monomer and subsequently air dried to produce a substrate giving grafted hydrophilic poly(ethylene oxide) groups.

Two functional polymerizable free radical active monomers comprising 1% VAZPIA photoinitiator and 5% 3-(Acryloxy)-2-hydroxypropylmethacrylate (Ac-Mac) are combined in methanol to make a coating solution that is imbibed into the hydrophilic PVDF membrane of Step 1 using the same procedures. The solution filled membrane is again subjected to an E-beam dose of 40 kGy set at a voltage of 300 keV, which also grafts these monomers to the surface of the PVDF substrate. After two minutes, the PET sandwich is opened and the grafted PVDF membrane is then allowed to air dry and not washed to produce a membrane having grafted photoinitiator groups and grafted methacrylate groups.

Ac-Mac, having a faster reacting acrylate monomer moiety is preferentially grafted to the support surface using the E-beam process. This allows most of the slower methacrylate moiety of AC-Mac to be free for later polymerization with the UV process. The photoinitiator VAZPIA is also grafted in Step 2. Therefore, these grafted chains have free radical active moieties and photoinitiator moieties on the same chain. In the third functionalizing step, a coating solution containing 10.0% vinyl dimethylazlactone-allyl amine adduct in 20% DI water, and 70% methanol was imbibed into the grafted TIPS PVDF microporous membrane of Steps 1 & 2. The porous film again was sandwiched "wet" between PET film and closed with any excess solution or trapped air bubbles removed with a roller. The sample was then UV irradiated using Quantum Technologies (Quant 48) system using UVA lamps and run under the UV processor at a speed of about one foot per minute (4 feet exposure length, single side at 31 mW/cm$^2$). The sample sandwich was turned over and run again at the same speed. After UV irradiation, the grafted porous membrane was removed from the sandwich and was washed by soaking it in a tray of water and exchanging it with clean water three times. The functionalized membrane was allowed to air dry. The resultant membrane has grafted dimethylazlactone-allyl amine adduct groups grafted to the surface of the substrate. Such grafting may be initiated by the free radical generated from the grafted photoinitator monomer, or from the methacrylate group of the grafted AcMac monomer. Again, the dimethylazlactone-allyl amine adduct may produce a grafted acrylate polymer having pendant —(CO)NHC(CH$_3$)$_2$(CO)NH—CH$_2$—CH=CH$_2$ groups from each acrylate polymer unit.

A 6 inch×7 inch sample of allyl-functional PVDF membrane was grafted with PEI according to the procedure of Example 3.

Examples 5-6

The PVDF porous substrate was imbibed with a solution containing 10.0 wt. % PEG 400 diacrylate monomer, SR-344™ and 90.0 wt. % methanol. The coated porous substrate was then placed 'wet' between two layers of polyethylene terephthalate (PET) film (first layer and second layer) having a thickness of approximately 100 micrometers. A removable first layer and a removable second layer were each placed on opposite sides of the coated porous substrate with any excess solution and trapped air bubbles squeezed out with a hand held rubber roller. The multilayer structure was conveyed through the electron beam on a carrier web. The multilayer structure was irradiated by electron beam (E-beam) on an ESI CB-300 electron beam with a dose of 20 kGy set at a voltage of 300 keV. Two minutes following irradiation, the hydrophilic functionalized porous substrate was removed from the first and second PET layers. The membrane was soaked in a tray of water that was exchanged two times with deionized water to wash the membrane of unreacted monomer and subsequently air dried The resulting hydrophilic membrane was then grafted a second time by each of the two alternate procedures:

Direct. The membrane was re-sandwiched and imbibed with a 20% solution of glycidyl methacrylate in methanol and passed through the electron beam, receiving a dose of 40 kGy at an accelerating voltage of 300 kV. The grafted membrane was removed and washed twice in isopropanol and dried.

Indirect. The membrane was inserted into a Ziploc bag in a glove box and sealed under an atmosphere of less than 40 ppm oxygen. The sealed bag was removed from the glove box and passed through the electron beam, receiving a dose of 40 kGy at a voltage of 300 kV. The sealed bag was re-conveyed into the glove box, opened under an atmosphere of less than 40 ppm oxygen and the membrane removed and placed into another, unirradiated Ziploc bag and imbibed with sufficient 20% glycidyl methacrylate (GMA) in methanol solution to wet the membrane. The bag was sealed to prevent evaporation and the imbibed membrane was allowed to sit for a period of 4 hours before being removed and washed twice in isopropanol and dried.

Approximately 6 inch×7 inch samples of oxirane-functional PVDF membranes were reacted with PEI by reaction with a 10% by weight solution of PEI in deionized water for 24 hours, then washed as indicated in Example 3 and allowed to air dry.

ΦX174 Clearance at 150 mM NaCl

| Example | Description | ΦX174 LRV |
|---|---|---|
| 3 | PEI/VDM allyl | 8.0 |
| 4 | PEI/VDM allyl | 8.1 |
| 5 | PEI/GMA (indirect) | 6.3 |
| 6 | PEI/GMA (direct) | 8.2 |

LRV results for the 50 mL fraction

What is claimed is:

1. An article comprising a substrate and extending from the surfaces thereof:
   grafted polyethyleneimine ligand groups forming a ligand-functionalized substrate;
   wherein the polyethyleneimine ligand groups are one or more of the formula:

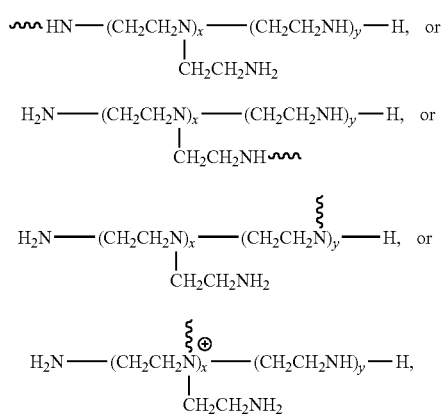

wherein:
   "~" is a divalent linking group grafted to the surface of the substrate and the polyethyleneimine ligand group,
   x may be zero and y is at least 1, and x+y is 2 to 50; and
   grafted quaternary ammonium groups on the surface of the substrate.

2. An article comprising a porous base substrate having interstitial and outer surfaces, grafted quaternary ammonium groups, and grafted ligand groups extending from the surfaces of the porous base substrate thereby forming a ligand-functionalized substrate; wherein the grafted ligand groups comprises the reaction product of a grafted electrophilic functional group and a ligand compound:

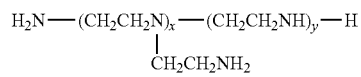

wherein x is zero, y is at least 1, and x+y is 2 to 2000.

3. An article comprising a substrate and extending from the surfaces thereof grafted polyethyleneimine ligand groups and grafted quaternary ammonium groups, thereby forming a ligand-functionalized substrate;
   wherein the polyethyleneimine ligand groups are one or more of the formula:

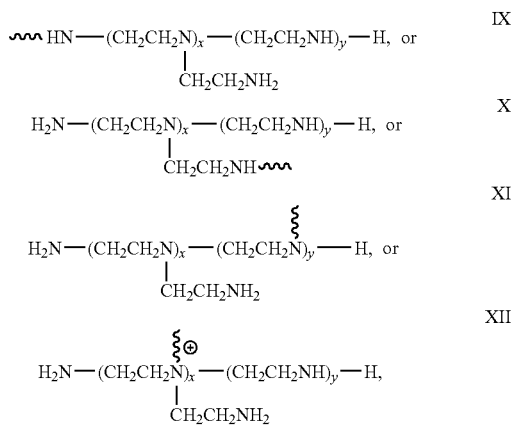

wherein:
   "~" is a divalent linking group grafted to the surface of the substrate and the polyethyleneimine ligand group,
   x may be zero and y is at least 1, and x+y is 2 to 50;
   wherein the ligand-functionalized substrate has enhanced binding selectivity for host cell proteins, DNA, RNA, and viruses relative to antibodies; and
   wherein the article yields a log-reduction value (LRV) of at least 5.0 for neutral viruses disposed in a solution comprising from 0 to about 150 mM salt.

* * * * *

UNITED STATES PATENT AND TRADEMARK OFFICE
CERTIFICATE OF CORRECTION

PATENT NO.        : 9,492,771 B2                                    Page 1 of 1
APPLICATION NO.   : 12/562573
DATED             : November 15, 2016
INVENTOR(S)       : Mark Etzel It is certified that error appears in the above-identified patent and that said Letters Patent is hereby corrected as shown below:

On the Title Page

Column 1, Item (65), under "Prior Publication Data," insert -- This application claims benefit of 61/098,337 filed 09/19/2008. --

Signed and Sealed this
Twenty-first Day of February, 2017

Michelle K. Lee
*Director of the United States Patent and Trademark Office*